United States Patent
Yamamoto et al.

(10) Patent No.: US 6,548,711 B2
(45) Date of Patent: Apr. 15, 2003

(54) PROCESS FOR PRODUCING 2-VINYLCYCLODODECANONE

(75) Inventors: Kenichi Yamamoto, Hiratsuka (JP); Misao Yagi, Hiratsuka (JP); Toshimitsu Hagiwara, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 44 days.

(21) Appl. No.: 09/876,231

(22) Filed: Jun. 8, 2001

(65) Prior Publication Data
US 2002/0038056 A1 Mar. 28, 2002

(30) Foreign Application Priority Data
Jun. 8, 2000 (JP) .......................... 2000-171974
May 9, 2001 (JP) .......................... 2001-138603

(51) Int. Cl.$^7$ .................... C07C 49/607; C07C 49/547
(52) U.S. Cl. ............................. 568/341; 568/338
(58) Field of Search .................... 568/341, 338

(56) References Cited

U.S. PATENT DOCUMENTS 3,923,699 A * 12/1975 Komatsu et al. ............... 512/2

FOREIGN PATENT DOCUMENTS

JP 78031147 * 8/1978 ............ B01J/27/10

* cited by examiner

Primary Examiner—Rosalynd Keys
(74) Attorney, Agent, or Firm—Kubovcik & Kubovcik

(57) ABSTRACT

A process for producing 2-vinylcyclododecanone, the process comprising isomerizing 2-ethylidenecyclododecanone represented by the following formula (1):

[Formula 1]

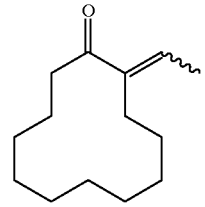

(1)

[Formula 1]

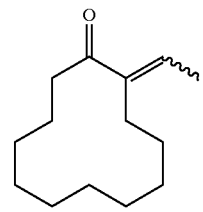

(1)

wherein the wavy line signifies that the double bond is a Z-isomer, an E-isomer or a mixture of an E-isomer and a Z-isomer; in the presence of a catalyst and separating 2-vinylcyclododecanone represented by the following formula (2) from the reaction product by fractionation:

[Formula 2]

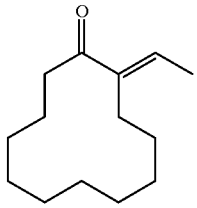

(2)

11 Claims, 3 Drawing Sheets

PROCESS FOR PRODUCING 2-VINYLCYCLODODECANONE

BACKGROUND OF THE INVENTION

1. Field of the Invention

The present invention relates to a novel process for producing 2-vinylcyclododecanone.

2. Description of the Related Art

2-Vinylcyclododecanone is a synthetic intermediate of 5-cyclohexadecen-1-one classified into a category of the musk perfumery in the perfumery field. Known methods of synthesizing this 2-vinylcyclododecanone include a method in which vinylmagnesium chloride is made to act on 2-chlorocyclododecan-1-one to obtain 2-chloro-1-vinylcyclododecan-1-ol, which is then heated in the presence of magnesium ethylbromide (publication of JP-A-49-49936), a method in which 2-vinylcyclododecene oxide is made to react in the presence of a Lewis acid catalyst (publication of JP-B-53-31147) and a method in which vinylmagnesium chloride is reacted with cyclododecene epoxide to prepare 2-vinylcyclododecan-1-ol, which is then oxidized (publication of JP-B-55-34780).

However, the method described in the publication of JP-A-49-49936 gives rise to a safety problem because this method uses, as a solvent, benzene, whose carcinogenicity has pointed out, in the final step as shown in the following reaction formula. Also, because a chloro-compound is used as a reaction raw material, there is a fear as to the safety of chlorides remaining when 5-cyclohexadecen-1-one is finally produced.

[Formula 3]

(2)

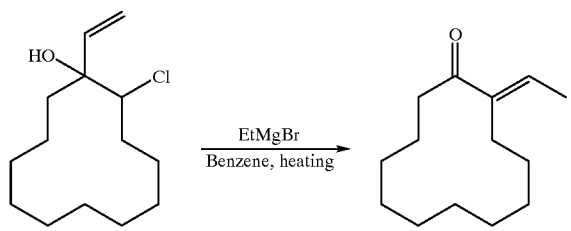

The method described in the publication of JP-B-53-31147, in turn, has the drawbacks that this method involves a water-washing step, solvent-recovery step and refining step, requiring complicated operations.

Also, the method described in the publication of JP-B-55-34780 is based on the reaction formula shown below. This method however has a low yield and benzene is used as a solvent, giving rise to a production problem.

[Formula 4]

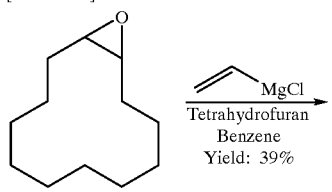

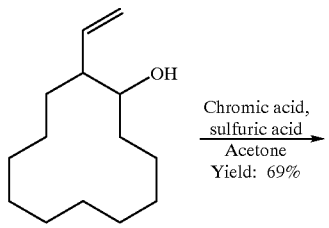

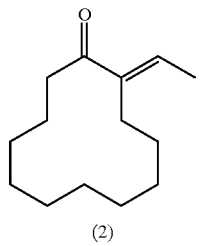

(2)

SUMMARY OF THE INVENTION

It is an object of the present invention to provide a process for producing 2-vinylcyclododecanone simply, efficiently and safely without involving any washing step, solvent recovery step and the like.

The inventors of the present invention have conducted earnest studies concerning a method of preparing 2-vinylcyclododecanone with high efficiency and, as a result, found that an equilibrium relation in terms of thermal isomerization is established between 2-ethylidenecyclododecanone and 2-vinylcyclododecanone, the isomerization equilibrium state can be reached in a short time by heating 2-ethylidenecyclododecanone in the presence of a specific isomerization catalyst, and 2-vinylcyclododecanone can be obtained with high efficiency if reaction distillation is further utilized. The present invention was thus completed.

Accordingly, the present invention provides a process for producing 2-vinylcyclododecanone, the process comprising isomerizing 2-ethylidenecyclododecanone represented by the following formula (1):

[Formula 5]

(1)

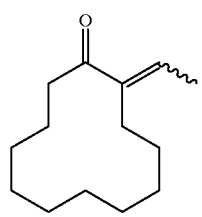

wherein the wavy line shows that the double bond is a Z-isomer, an E-isomer or a mixture of an E-isomer and a Z-isomer; in the presence of a catalyst and separating 2-vinylcyclododecanone represented by the following formula (2) from the reaction product by fractionation:

[Formula 6]

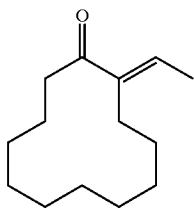

(2)

DETAILED DESCRIPTION OF THE PREFERRED EMBODIMENTS

Figure 1:
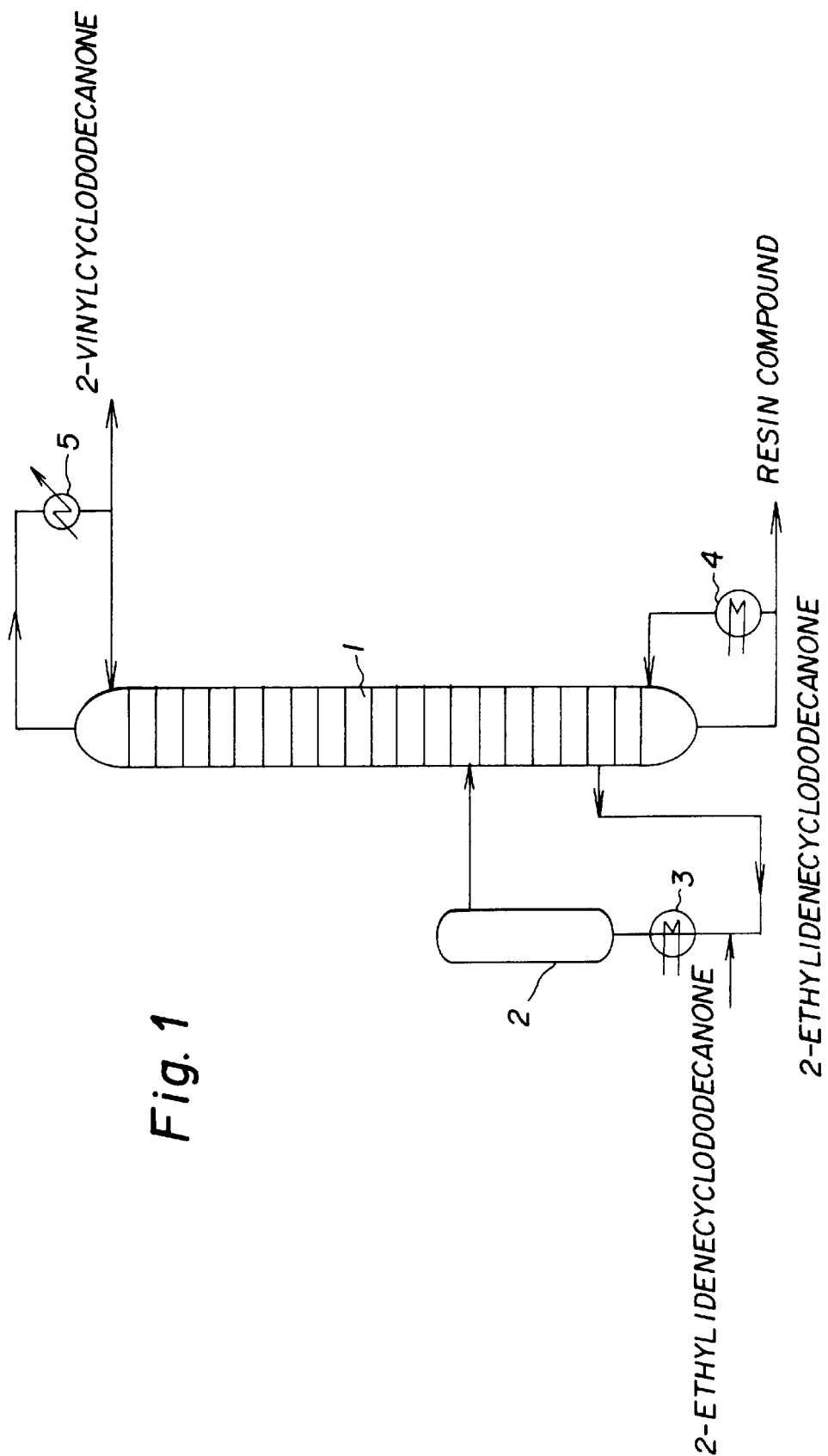
FIG. 1 is a schematic view of a reaction distiller comprising a combination of a reaction vessel and a BETRYUKU continuous distillation tower.

In the process of the production of 2-vinylcyclododecanone according to the present invention, 2-ethylidenecyclododecanone is heated in the presence of a specific catalyst to establish an isomerization equilibrium state between 2-(E)-ethylidenecyclododecanone (1-a), 2-(Z)-ethylidenecyclododecanone (1-b) and 2-vinylcyclododecanone (2) in a short time as shown below and 2-vinylcyclododecanone as a reaction product is separated by fractionation thereby producing 2-vinylcyclododecanone.

[Formula 7]

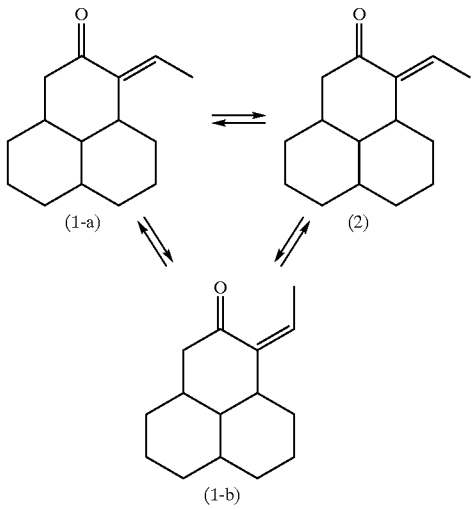

Here, the abundance ratio between 2-(E)-ethylidenecyclododecanone (1-a), 2-(Z)-ethylidenecyclododecanone (1-b) and 2-vinylcyclododecanone (2) when the equilibrium state is reached are as follows: $^2$-(E)-ethylidenecyclododecanone (1-a) : 94% to 91%, $^2$-(Z)-ethylidenecyclododecanone (1-b): 5.5% to 7.9% and 2-vinylcyclododecanone (2): 0.5% to 1.1% at temperatures ranging from 200° C. to 250° C. The higher the temperature is, the larger the abundance ratio of intended 2-vinylcyclododecanone when equilibrium is reached (Table 1) larger the rate of isomerization becomes.

TABLE 1

| Isomerization temperature (° C.) | Abundance ratio of 2-vinylcyclododecanone when equilibrium is reached |
|---|---|
| 200 | 0.5 (%) |
| 250 | 1.1 (%) |
| 300 | 1.7 (%) |

Although such isomerization from 2-ethylidenecyclododecanone to 2-vinylcyclododecanone proceeds only heat energy, the rate is very low. The rate of isomerization is outstandingly improved if a catalyst is used as shown in Example 1.

On the other hand, 2-vinylcyclododecanone (2) which is the object product is one having the lowest boiling point among the components of the equilibrated mixture. Specifically, the average relative volatility of each of these components is as follows though it varies depending on temperature: when the boiling point is 110° C., the average relative volatility of each of 2-(Z)-ethylidenecyclododecanone (1-b) and 2-vinylcyclododecanone (2) is 1.15 and 1.44, respectively provided that the average relative volatility of 2-(E)-ethylidenecyclododecanone (1-a) is defined as 1.00.

Therefore, this equilibrium can be shifted to the side of 2-vinylcyclododecanone (2) which is an object product by distillation separation using a distillation tower. To state concretely, making use of reaction distillation, 2-vinylcyclododecanone as the product is separated from 2-ethylidenecyclododecanone as the raw material and then led to an external system whereby 2-vinylcyclododecanone can be produced efficiently.

The isomerization reaction using the catalyst according to the present invention is run using no solvent wherein 2-ethylidenecyclododecanone as a reaction substrate itself works as a solvent. Therefore, a reaction using no solvent is practical in consideration of the separation of the product after the reaction is completed. However, one or two or more types among hydrocarbon type solvents, ether type solvents and aromatic type solvents, such as paraffin, polyethylene, polyethylene glycol dimethyl ether and NeoSK-OIL (manufactured by Soken Formula), having a higher boiling point than $^2$-ethylidenecyclododecanone may be used according to need. In this case, the amount of the solvent to be used is 0.5 times by weight to 20 times by weight and, preferably, 1 time to 5 times the amount of 2-ethylidenecyclododecanone in consideration of, particularly, economy and reactivity.

The reaction temperature in the isomerization reaction is 150° C. to 350° C. and, appropriately, 175° C. to 250° C. in consideration of, particularly, economy and reactivity. The abundance ratio of 2-vinylcyclododecanone is increased with increased temperature. However, an isomerization reaction temperature of 350° C. or more causes the concurrence of a side reaction and is hence undesirable.

Also, no particular limitation is imposed on the reaction pressure and the reaction may be run under pressure or reduced pressure and, preferably, under reduced pressure.

As the catalyst in the present invention, catalysts which are usually used for the isomerization of olefins may be used. Because there is a case where this reaction is associated with one of the shift of a double bond to the inside of a ring and a disproportionation reaction or both side reactions depending on the type of catalyst when the reaction is run as shown in the following reaction formula, a catalyst which does not cause such side reactions must be selected. From this point of view, preferable examples of the catalyst include acid catalysts, solidbase catalysts, metal catalysts on a support, homogeneous metal complexes and catalysts of organic acid-alkali metal salts.

catalyst, calcium hydroxide-zirconium oxide catalyst, barium hydroxide-zirconium oxide catalyst, sodium carbonate-zirconium oxide catalyst, potassium carbonate-zirconium oxide catalyst, cesium carbonate-zirconium oxide catalyst, rubidium carbonate-zirconium oxide catalyst, sodium bicarbonate-zirconium oxide catalyst, potassium bicarbonate-zirconium oxide catalyst, sodium hydroxide-silica gel catalyst, potassium hydroxide-silica gel catalyst, lithium hydroxide-silica gel catalyst, cesium hydroxide-silica gel catalyst, rubidium hydroxide-silica gel catalyst, calcium hydroxide-silica gel catalyst, barium hydroxide-

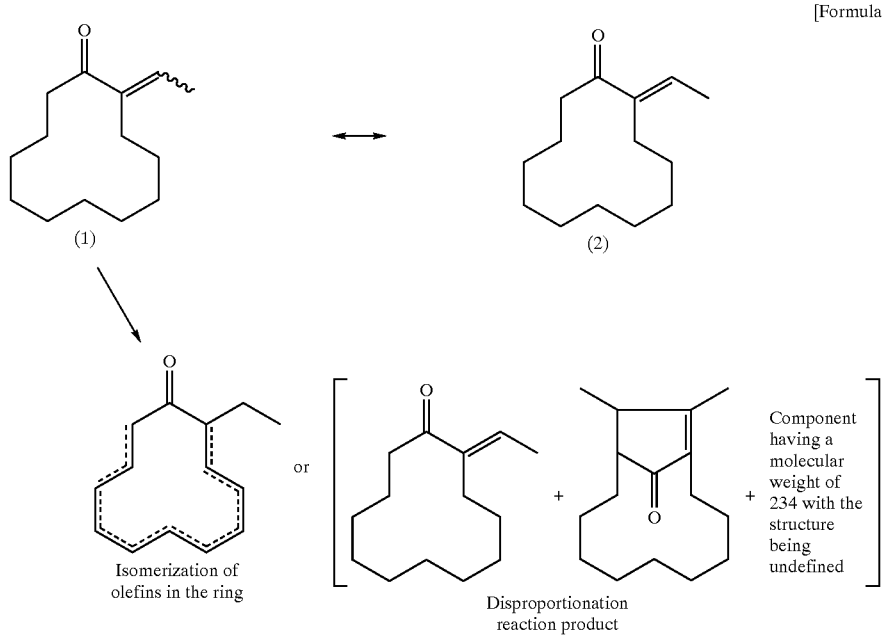

[Formula 8]

wherein the wavy line shows that the double bond is a Z-isomer, an E-isomer or a mixture of an E-isomer and a Z-isomer.

As examples of the acid catalyst, a general Brønsted acid or a solid acid is given. Examples of the Brønsted acid include paratoluenesulfonic acid or sulfuric acid and examples of the solid acid include silica alumina, sulfuric acid-zirconium oxide and niobic acid. The solid acid catalyst may be a powder or a molded product. The amount of such a catalyst to be used is 0.1% by weight to 50% by weight and, preferably, 1% by weight to 20% by weight based on 2-ethylidenecyclododecanone used as starting material in consideration of, particularly, economy and reactivity.

Examples of the solid base catalyst include supported catalysts in which a hydroxide or carbonate of an alkali metal or alkali earth metal is carried on a support. Here, examples of the support include silica gel, alumina, carbon, zirconium oxide and titanium oxide.

Specific examples of such catalysts with a support include the following catalysts obtained by mixing an aqueous solution of sodium hydroxide, potassium hydroxide, lithium hydroxide, cesium hydroxide, rubidium hydroxide, calcium hydroxide, barium hydroxide, sodium carbonate, potassium carbonate, cesium carbonate, rubidium carbonate, sodium bicarbonate, sodium bicarbonate or potassium bicarbonate with silica gel or zirconium oxide, followed by calcinating. Specifically, given as examples of these catalysts are a sodium hydroxide-zirconium oxide catalyst, potassium hydroxide-zirconium oxide catalyst, lithium hydroxide-zirconium oxide catalyst, cesium hydroxide-zirconium oxide catalyst, rubidium hydroxide-zirconium oxide silica gel catalyst, sodium carbonate-silica gel catalyst, potassium carbonate-silica gel catalyst, cesium carbonate-silica gel catalyst, rubidium carbonate-silica gel catalyst, sodium bicarbonate-silica gel catalyst and potassium bicarbonate-silica gel catalyst.

The amount of a hydroxide or carbonate of an alkali metal or alkali earth metal to be carried is 0.1% by weight to 50% by weight and, preferably, 0.1% by weight to 10% by weight in consideration of reactivity. Calcinating temperature when these catalysts are produced by calcination is 100° C. to 1000° C. and preferably 200° C. to 700° C. in consideration of reactivity. This calcinating operation may be carried out under reduced pressure, in an inert gas stream or in a dry air stream.

Besides the aforementioned supported catalysts, metal oxides such as magnesium oxide, calcium oxide and titanium oxide are given as examples of the solid base catalyst. It is to be noted that the metal oxide such as magnesium oxide is produced by calcinating commercially available magnesium oxide or magnesium hydroxide by using a usual method and used for the reaction.

The amount of such a solid base catalyst to be used is 0.1% by weight to 50% by weight and, preferably, 1% by weight to 20% by weight based on 2-ethylidenecyclododecanone used as starting material in consideration of, particularly, economy and reactivity.

Also, when such a solid base catalyst is used, an alcohol having a molecular weight of 100 or more may be added for the purpose of improving reaction selectivity. There is no particular limitation to the type of alcohol as far as it has a molecular weight of 100 or more. Examples of the alcohol include polyethylene glycol 200, polyethylene glycol 400, polyethylene glycol 600, myoinositol, and 1,1,1-tris (hydroxymethyl) ethane. Several types of alcohol may be mixed. Among these alcohols, particularly polyethylene glycol is preferable in consideration of economy and reactivity.

The amount of the alcohol to be used is 0.1% by weight to 200% by weight and, particularly, preferably 0.5 to 50% by weight based on 2-ethylidenecyclododecanone.

Examples of the metal catalyst on a support include those obtained by carrying each metal belonging to the transition metals 7, 8 and 9 of the elemental periodic chart (recommended by IUPAC in 1997), preferably, ruthenium, rhenium or rhodium and, more preferably, ruthenium or rhenium on alumina, silica gel, carbon, titanium oxide or the like. Also, the ratio of the metal carried on the support to the support is 0.1% by weight to 20% by weight and, preferably, 1% by weight to 7% by weight, in consideration of, particularly, economy and reactivity.

The amount of the metal catalyst on a support is 0.1% by weight to 50% by weight and, preferably, 1% by weight to 20% by weight based on 2-ethylidenecyclododecanone used as starting material in consideration of, particularly, economy and reactivity.

The above metal catalyst on a support may also be used after it is treated by oxidation. As examples of catalysts prepared by oxidizing a ruthenium with a support, and catalysts which are produced by carrying ruthenium on silica gel and then treating the resulting product by using air or oxygen are given. The temperature of the oxidizing treatment when the ruthenium-silica catalyst is oxidized is 10° C. to 500° C. and, particularly preferably, 20° C. to 250° C. Treating time is 0.5 hours to 720 hours and, particularly preferably, 1 hour to 240 hours though it differs depending on the temperature and the density of oxygen. The ratio of ruthenium carried on the support to the support is 0.1% by weight to 20% by weight and preferably 1% by weight to 7% by weight in consideration of, particularly, economy and reactivity. The amount of the catalyst is the same as in the case of the metal catalyst on a support.

The configuration of the solid catalyst shown as above may be a molded product or a powder. Also, the above catalysts may be used either singly or by mixing two or more.

Examples of the homogeneous metal complex include a ruthenium phosphite complex, ruthenium phosphine complex, rhodium phosphate complex and rhodium phosphine complex.

Such a homogeneous metal complex can be prepared using a $[MX_2(Y)]_2$ complex as starting material. Here, M represents a metal, X represents a halogen atom and Y represents an allene compound. Although the halogen atom among them may be chlorine, bromine or iodine, chlorine or bromine is preferable in consideration of economy and reactivity. Given as examples of the allene compound represented by Y are paracymene, xylene and benzene.

Specifically, a phosphine or phosphites were added as a ligand to $[MX_2(Y)_2]$ in the presence of a solvent such as acetonitrile or benzonitrile under a nitrogen atmosphere in an amount of 1 to 20 equivalent mols and, preferably, 2 to 10 equivalent mols. The mixture was stirred under heating to obtain a pale yellowish uniform catalyst solution. As the ligand, triphenylphosphine, triphenyl phosphite, bisdiphenylphosphonylalkane $((Ph)_2P(CH_2)_nP(Ph)_2$, n=2 to 6) and bisallyl phosphites $((PhO)_2PO(CH_2)_nOP(OPh)_2$, n=2 to 6) may be used (where Ph represents a phenyl group and OPh represents a phenoxy group). Temperature for the preparation is 50° C. to 300° C. and, preferably, 100° C. to 250° C. Time for the preparation of the catalyst is 0.1 to 10 hours and, preferably, 0.1 hour to 3 hours. The catalyst solution obtained in this manner is used for the isomerization reaction as it is or after a solvent is removed.

The amount of the homogeneous metal complex is 0.01% by weight to 10% by weight and, preferably, 0.1% by weight to 5% by weight in consideration of, particularly, economy and reactivity.

The organic acid used to prepare the alkali metal salt catalyst of the organic acid may be either an aliphatic type or an aromatic type. For example, examples of the aliphatic type include acetic acid, propionic acid and decanoic acid and examples of the aromatic type include benzoic acid and naphthenic acid though there is no limitation to these acid types. As the alkali metal, hydroxides or carbonates of sodium, potassium, cesium or rubidium may be used. The alkali metal salt catalyst of an organic acid may be prepared by mixing the organic acid with an equivalent mol of an hydroxide or carbonate of an alkali metal in an alcohol type organic solvent such as methanol and ethanol. The catalyst solution obtained in this manner is used for the isomerization reaction as it is or after a solvent is removed. The amount of the alkali metal salt catalyst of an organic acid is preferably 0.001% by weight to 2% by weight based on 2-ethylidenecyclododecanone used as starting material.

2-Ethylidenecyclododecanone is isomerized under heating by using the above isomerization catalyst and thereafter 2-vinylcyclododecanone is separated from the reaction product by fractionation by means of distillation or the like. However, isomerization and distillation using a reaction distiller are carried out at the same time to separate 2-vinylcyclododecanone from the other two components and the separated 2-vinylcyclododecanone is removed from the system. This enables the production of 2-vinylcyclododecanone with high efficiency.

Figure 2:
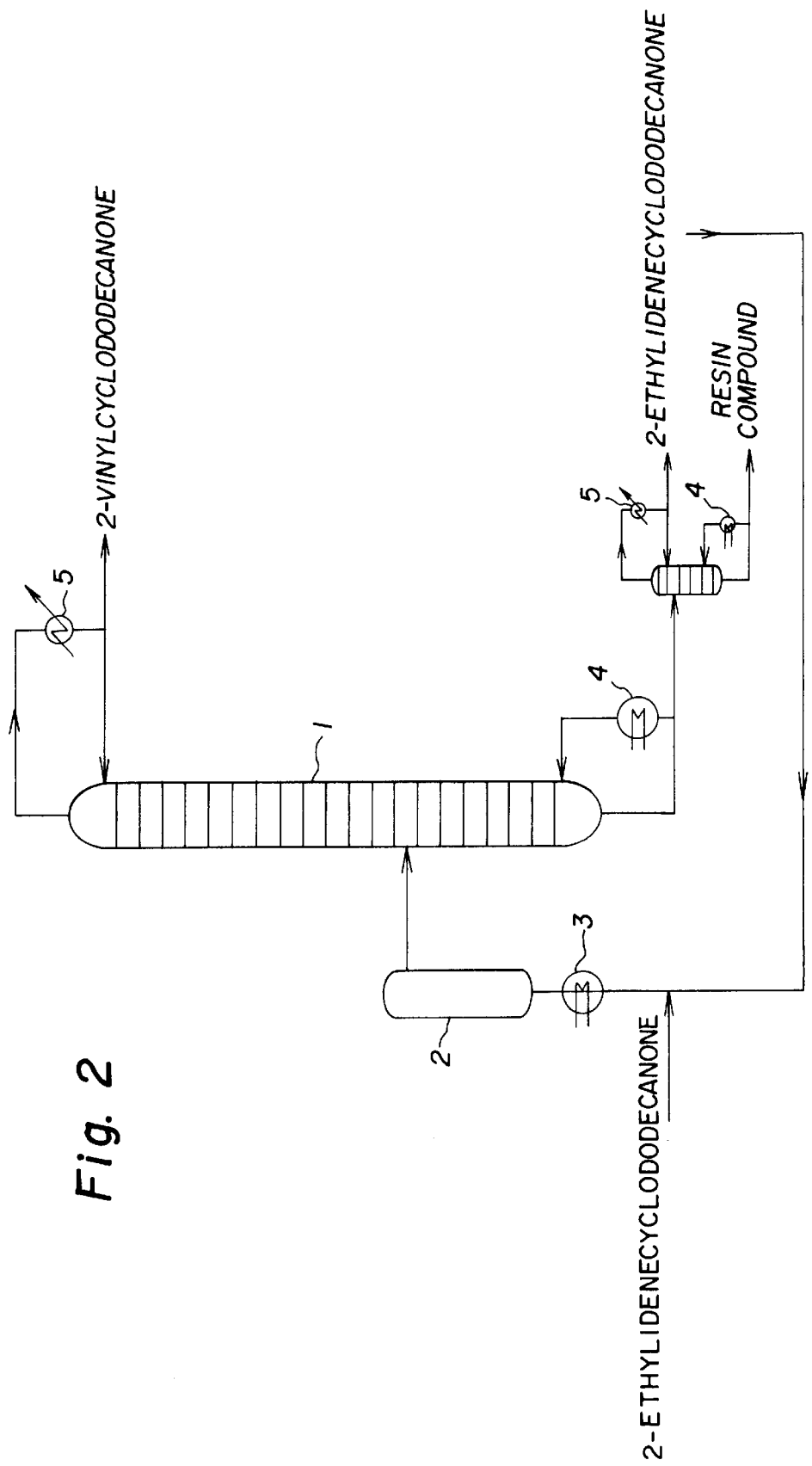
FIG. 2 is a schematic view of a reaction distiller comprising plural combinations of a reaction vessel and a continuous distillation tower.
Figure 3:
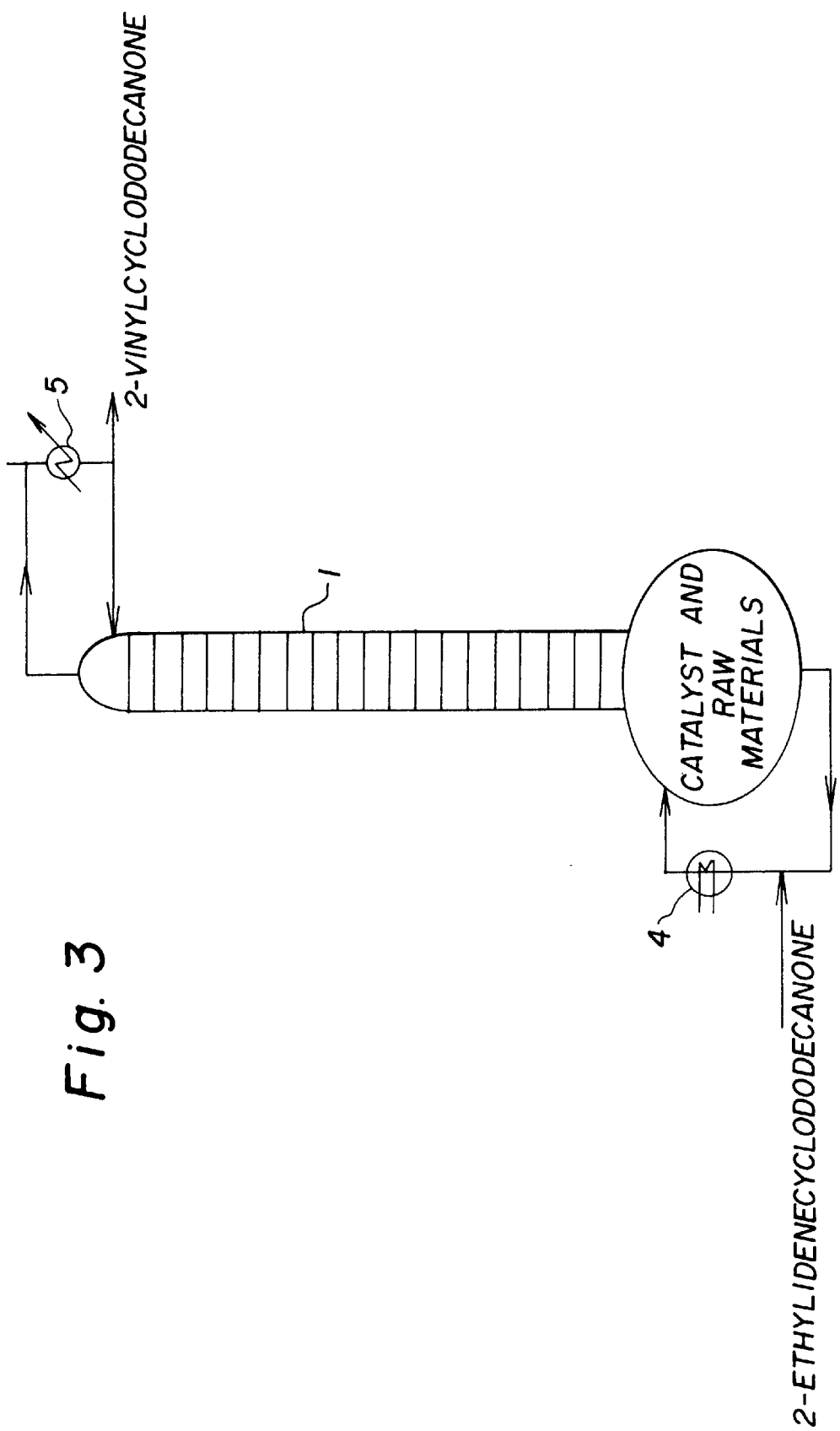
FIG. 3 is a schematic view of a reaction distiller in which a reaction vessel is integrated with a distiller.

There is no particular limitation as to the reaction distiller as far as it has a structure provided with a reaction kettle equipped with a distiller used for general distillation refining and can separate the product, 2-vinylcyclododecanone from the raw material, 2-ethylidenecyclododecanone. Examples of the reaction distiller include a reactor obtained by combining a reaction vessel filled with a catalyst with a BETRYUKU type continuous distillation tower as shown in FIG. 1, a reactor obtained by combining a reaction vessel filled with a catalyst with continuous distillation towers as shown in FIG. 2 and a reactor in which a reaction vessel filled with a catalyst and a distillation tower are integrated with each other as shown in FIG. 3.

Here, there is no particular limitation to a packing of the distillation tower as far as it can be generally used for distillation. For example, a heli-pak, pole ring or Sulzer packing may be used. A pole ring is more preferable in consideration of, particularly, economy.

The vacuum at the top of the distillation tower is in a range from 13 Pa to 13300 Pa and preferably 13 Pa to 5320 Pa in consideration of, particularly, reactivity though it differs depending on the type of equipment and the isomerization reaction temperature.

Also, if the number of stages in the distillation tower is 60 or more, the object 2-vinylcyclododecanone can be perfectly separated from 2-ethylidenecyclododecanone. If the number of stages is 60 or less, only imperfect separation is made. Therefore, reaction distillation and refining distillation may be carried out separately.

EXAMPLES

The present invention will be hereinafter explained in more detail by way of examples.

Example 1

Synthesis of 2-vinylcyclododecanone

A temperature gage was attached to a 30 ml round bottom flask provided with a stirring rotor. The round bottom flask was charged with 10g of 2-ethylidenecyclododecanone (purity: 99.2%) and 0.10 g of the catalyst shown in the following table. After the air in the reactor was replaced with nitrogen, the mixture was heated to 200° C. and stirred to run a reaction. After 2.5 minutes, 5 minutes, 10 minutes, 20 minutes, 40 minutes, 80 minutes and 160 minutes, samples of the reaction mixture were respectively taken and subjected to gas chromatography analysis (column: HP-5, 30 m×0.32 mm×0.25 μm, temperature rise condition: 150° C.-2° C./min–230° C.). The time required for all three components consisting of 2-vinylcyclododecanone which is the object product, and the other two components, namely, 2-(Z)-ethylidenecyclododecanone and 2-(E)-ethylidenecyclododecanone, to reach an isomerization equilibrium state was examined. Also, for a comparative example, the result obtained when 2-ethylidenecyclododecanone was isomerized by only heat without using any catalyst is shown in Table 2 below.

TABLE 2

| Catalyst | Time required to reach an isomerization equilibrium state (hr) |
|---|---|
| Paratoluenesulfonic acid[1] | 0.5 |
| Silica alumina[2] | 1.5 |
| Sulfuric acid-zirconium oxide[3] | 1.0 |
| 3% sodium hydroxide-silica gel[4] | 0.17 |
| 3% potassium hydroxide-silica gel[4] | 0.67 |
| Magnesium oxide[5] | 0.05 |
| Magnesium oxide + polyethylene glycol 400[5]@ | 0.08 |
| 5% rhenium-silica gel[6] | 10 |
| 5% ruthenium-silica gel[6] | 0.17 |
| 5% ruthenium-silica gel-oxide[6] | 0.33 |
| [RuClP(OPh)$_2$(p-cymene)(PhCN)]Cl[7] | 1.0 |
| Cesium naphthenate[8] | 0.05 |
| Heat (200° C., no catalyst) | 48 |

@: The amount of polyethylene glycol 400 was 1% by weight based on 2-ethylidenecyclododecanone.
[1]Paratoluenesulfonic acid: manufactured by NacalaiTesque, Inc.
[2]Silica alumina: manufactured by Fuji Silysia Chemical Ltd.
[3]Sulfuric acid-zirconium oxide: manufactured by Japan Energy.
[4]3% sodium hydroxide-silica gel and 3% potassium hydroxide-silica: produced as follows: a 50 ml beaker was charged with 0.2 g of sodium hydroxide or potassium hydroxide and 9.8 ml of water to prepare an aqueous 2% solution, to which was added 7.0 g of silica gel manufactured by NacalaiTesque, Inc. and the mixture was placed in an electric furnace and calcined at 500° C. under a reduced pressure of 2700 Pa.
[5]Magnesium oxide: manufactured by KANTO KAGAKU.
[6]5% rhenium-silica gel, 5% ruthenium-silica gel and 5% ruthenium-silica gel-oxide: manufactured by N · E Chemcat.
[7][RuClP(OPh)$_2$(p-cymene)(PhCN)]Cl: a 200 ml round bottom flask equipped with a temperature gage and a stirring unit was charged with 0.15 g of di-μ-chloro-bis[(p-cymene-2-yl)ruthenium (II) chloride]. After the air in the flask was replaced with nitrogen, 10 ml of benzonitrile and 0.31 g of triphenyl phosphite were compounded in the mixture and the resulting mixture was heated at 190° C. with stirring for 10 minutes. Then, a solvent was removed under reduced pressure to produce a powder of a catalyst (0.45 g).
[8]Cesium naphthenate: a 200 ml reaction flask was charged with 5.487 g of cesium carbonate (cesium: 33.68 mM), to which was added 50 ml of methanol to dissolve cesium carbonate. 50 ml of a methanol solution containing 10 g of naphthenic acid (Mitsui Petrochemical: NSA-185) was gradually added from a dropping funnel. A uniform methanol solution of cesium naphthenate was thus obtained.

Example 2

Synthesis of 2-vinylcyclododecanone

A 500 ml reaction round bottom flask provided with a stirring rotor was equipped with a temperature gage and a distiller comprising a glass pipe having a diameter of 25 mm and a height of 550 mm and is filled with a Sulzer laboratory packing (manufactured by Sumitomo Heavy Industries, Ltd.) corresponding to 20 stages. This round bottom flask was charged with 150 g of 2-ethylidenecyclododecanone (purity: 99.2%) and 7.5 g of a silica alumina catalyst (5% by weight, manufactured by Fuji Silysia Chemical Ltd.) and the mixture was heated with stirring under reduced pressure to carry out reaction distillation. The degree of vacuum at the top of the distiller was adjusted to around 5×10³ Pa such that the liquid temperature in the flask was around 200° C. Total refluxing is performed to stabilize the material composition in the distiller for one hour after the liquid reached the top of the distiller. After that, the reaction product flowed out at a rate of about 8 g per hour. The distillate which is the reaction product contained about 20% by weight of 2-vinylcyclododecanone which is the object product, about 25% by weight of 2-(Z)ethylidenecyclododecanone and about 55% by weight of 2-(E)-ethylidenecyclododecanone. This reaction product was placed in a rounded bottom flask equipped with a temperature gage and a distiller provided with a glass pipe having a diameter of 25 mm and a height of 550 mm and is filled with a Sulzer laboratory packing corresponding to 20 stages to fractionate the reaction product into 2-vinylcyclododecanone and other compounds. Because 2-(Z)-ethylidenecyclododecanone and 2-(E)-ethylidenecyclododecanone can be reused as the raw materials, the both were returned to the 500 ml reaction rounded bottom flask equipped with the aforementioned distiller and reaction distillation continued.

The product generated by reaction distillation is separated into 2-vinylcyclododecanone as the object product and 2-(Z)-ethylidenecyclododecanone and 2-(E)-ethylidenecyclododecanone which can be reused as the raw materials and the latter two components were recycled repeatedly. Thus 2-vinylcyclododecanone was obtained in an amount of 110 g (theoretical yield: 73%).

(1) Physical Data of 2-vinylcyclododecanone $^1$H-NMR (500 MHz, CDCl$_3$, ppm):
5.80(1H, ddd, J=8.3, 10.2, 17.3Hz), 5.14(1H, dt, 17.3, 1.1), 5.09(1H, dm, 10.2), 3.37(1H, ddd, 3.3, 8.3, 10.7), 2.57(1H, ddd, 3.3, 7.4, 15.7), 2.42(1H, ddd, 3.5, 10.7, 15.7), 1.96(1H, m), 1.82(1H, m) 1.61(1H, m), 1.47(1H, m), 1.42-1.19(14H, m)

$^{13}$C-NMR (125MHz, CDCl$_3$, ppm):
212.29(s), 136.88(d), 116.69(t), 55.81(d), 38.24(t), 30.23(t), 25.42(t), 24.90(t), 24.61(t), 24.49(t), 24.22(t), 23.16(t), 22.28(t), 22.20(t)

IR(neat, cm$^{-1}$)
2931, 2864, 1709, 1633, 1469, 1444, 1414, 1360, 994, 917

MS (EI, m/z):
208(M+, 28), 193(3), 179(9), 165(21), 151(17), 137(21), 123(15), 111(41), 98(100), 81(72), 67(83), 55(100), (2) Physical Data of 2-(Z)-ethylidenecyclododecanone $^1$H-NMR (500 MHz, CDCl$_3$, ppm):
5.72(1H, q, J=7.4Hz), 2.63(2H,m), 2.34(2H,t, 5.9), 1.78(3H, d, 7.4), 1.75(2H, m), 1.42-1.18(14H, m)

$^{13}$C-NMR (125MHz, CDCl$_3$, ppm):
208.20(s), 143.30(s), 129.07(d), 40.58(t), 34.17(t), 25.78(t), 25.70(t), 25.38(t), 25.05(t), 24.89(t), 24.88(t), 23.03(t), 22.67(t), 15.38(q)

IR (neat, cm$^{-1}$):
2930, 2863, 1695, 1668, 1468, 1444, 1384, 1367

MS (EI, m/z):
208(M+, 100), 193(39), 175(10), 165(17), 151(31), 137(55), 123(65), 109(74), 95(77), 81(73), 67(72), 55(84), 41(66)

(3) Physical Data of 2-(E)-ethylidenecyclododecanone $^1$H-NMR (500 MHz, CDCl$_3$, ppm):
6.65(1H, q, J=6.9Hz), 2.68(2H,m), 2.42(2H, t, 5.9), 1.86(3H, d, 6.9), 1.67(2H, m), 1.42-1.18(14H, m)

$^{13}$C-NMR (125MHz, CDCl$_3$, ppm):

204.66(s), 142.29(s), 136.83(d), 38.39(t), 26.45(t), 26.41(t), 24.81(t), 24.41(t), 24.31(t), 24.29(t), 23.75(t), ,23.06(t), 22.65(t), 14.78(q)

IR (neat, cm$^{-1}$):

2930, 2863, 1665, 1639, 1468, 1444, 1384, 1266, 1237

MS (EI, m/z):

208(M+, 100), 193(49), 175(15), 165(28), 151(55), 137(89), 123(93), 109(92), 95(89), 81(82), 67(82), 55(92), 41(75)

Example 3
Synthesis of 2-vinylcyclododecanone

2-Vinylcyclododecanone was obtained in an amount of 128.7 g (theoretical yield: 85.8%) by using the same method as in Example 2 except that a catalyst produced by dipping 7.0 g of silica in 10 g of an aqueous 2% sodium hydroxide solution and then calcinating the mixture at 500° C. under a reduced pressure of 2.7×10$^3$ Pa for 3 hours was used in place of the silica alumina catalyst.

Example 4
Synthesis of 2-vinylcyclododecanone

2-Vinylcyclododecanone was obtained in an amount of 109.2 g (theoretical yield: 72.8%) by using the same method as in Example 3 except that 150 g of paraffin (having a boiling point of about 370° C. under normal pressure) having a melting point of 42° C. to 44° C., was compounded as the high boiling point solvent. The use of the high boiling point solvent caused a rise in boiling point, with the result that the degree of vacuum at the top of the distiller was decreased to 2.7×10$^3$ Pa.

Example 5
Synthesis of 2-vinylcyclododecanone

2-Vinylcyclododecanone was obtained in an amount of 30 g (theoretical yield: 20%) by using the same method as in Example 2 except that magnesium oxide (manufactured by KANTO KAGAKU) was used in place of the silica alumina catalyst.

Example 6
Synthesis of 2-vinylcyclododecanone

2-Vinylcyclododecanone was obtained in an amount of 119.4 g (theoretical yield: 79.6%) by using the same method as in Example 5 except that polyethylene glycol 400 (manufactured by NacalaiTesque, Inc. was added in an amount of 5% by weight based on the raw material for the purpose of improving reaction selectivity.

Example 7
Synthesis of 2-vinylcyclododecanone

2-Vinylcyclododecanone was obtained in an amount of 136.6 g (theoretical yield: 91.1%) by using the same method as in Example 2 except that a catalyst (manufactured by N•E Chemcat) obtained by carrying 5% ruthenium on silica gel was used in place of the silica alumina catalyst.

Example 8
Synthesis of 2-vinylcyclododecanone

2-Vinylcyclododecanone was obtained in an amount of 136 g (theoretical yield: 90.7%) by using the same method as in Example 2 except that a catalyst (manufactured by N•E Chemcat) obtained by carrying 5% ruthenium on silica gel, followed by oxidizing treatment was used in place of the silica alumina catalyst.

Example 9
Synthesis of 2-vinylcyclododecanone

2-Vinylcyclododecanone was obtained in an amount of 90 g (theoretical yield: 60%) by using the same method as in Example 2 except that a [RuClP(OPh)$_2$ (p-cymene) (PhCN)]Cl catalyst whose preparation method was described in Example 1 was used in place of the silica alumina catalyst.

Example 10
Synthesis of 2-vinylcyclododecanone

2-Vinylcyclododecanone was obtained in an amount of 142 g (theoretical yield: 94.7%) by using the same method as in Example 2 except that a methanol solution of a cesium naphthenate catalyst whose preparation method was described in Example 1 was used in place of the silica alumina catalyst.

Comparative Example 1

A trial was made to isomerize 2-ethylidenecyclododecanone to 2-vinylcyclododecanone by using the isomerization reaction used to transform a conjugate ketone into a non-conjugate ketone using t-BuOK as described in the publication of JP-A-10-36298.

Specifically, 1.12 g (0.01 mol) of t-BuOK was dissolved in tetrahydrofuran (15 ml), to which was then added 2.08 g (0.01 mol) of 2-ethylidenecyclododecanone and the mixture was stirred at room temperature for 30 minutes. Thereafter, the reaction mixture was poured into 15 ml of an aqueous ammonium chloride solution. After usual finish treatment was performed, a crude product was obtained in an amount of 2.10 g. The crude product contained 20% of 2-vinylcyclododecanone.

As a result, 2-vinylcyclododecanone was obtained in a yield of 20%, but the aforementioned disproportionation reaction product was a major product (80%) and also, t-BuOK was used in an amount by mol equivalent to the substrate. Therefore, this method was judged to be unadaptable to the production of 2-vinylcyclododecanone.

Comparative Example 2

A trial was made to isomerize 2-ethylidenecyclododecanone to 2-vinylcyclododecanone on the basis of the method of the isomerization of a double bond by using light as described in J. Chem. Soc. [C] 1966, 571.

Specifically, 2-ethylidenecyclododecanone was placed in a Pyrex reaction container and irradiated with light for 2 hours by using a high pressure mercury lamp (having a discontinuous wavelength ranging from about 250 nm to 580 nm) manufactured by SEN LIGHTS CORPORATION. The temperature of the inside of the reaction container at this time was about 200° C. to 240° C. The reaction product was cooled to ambient temperature and then subjected to gas chromatography analysis (column: HP-5, 30 m×0.32 mm×0.25 μm, temperature rise condition: 150° C.-2° C./min-230° C). The ratio between 2-vinylcyclododecanone, 2-(Z)-ethylidenecyclododecanone, 2-(E)-ethylidenecyclododecanone and other unidentified compounds was 0.16:44.66:52:3.18.

As a result, 2-vinylcyclododecanone was produced in an amount of only 0.16% for a reaction time of 2 hours. Therefore, this method was less efficient in the isomerization of 2-ethylidenecyclododecanone to 2-vinylcyclododecanone and was judged to be unadaptable to the production of 2-vinylcyclododecanone.

According to the production process of the present invention, 2-vinylcyclododecanone can be produced using 2-ethylidenecyclododecanone, which can be manufactured simply from cyclododecanone in a high yield through no chlorination, without using any solvent which has a safety problem in a high yield by using a simple process involving neither washing nor solvent recovery.

What is claimed is:

1. A process for producing 2-vinylcyclododecanone, the process comprising heating 2-ethylidenecyclododecanone represented by the following formula (1):

[Formula 1]

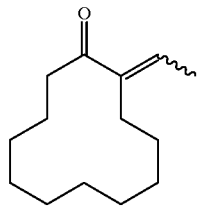

(1)

[Formula 1]

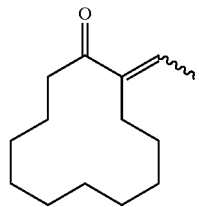

(1)

wherein the wavy line signifies that the double bond is a Z-isomer, an E-isomer or a mixture of an E-isomer and a Z-isomer; in the presence of a catalyst to establish an isomeration equilibrium state between said Z-isomer, E-isomer and 2-vinylcyclodecanone represented by the following formula (2) and separating the 2-vinylcyclododecanone from the reaction product by fractionation:

[Formula 2]

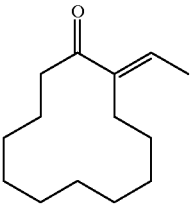

(2)

2. The process for producing 2-vinylcyclododecanone according to claim 1, wherein the separation of 2-vinylcyclododecanone by fractionation is carried out by reaction distillation.

3. The process for producing 2-vinylcyclododecanone according to claim 1, wherein the catalyst is one or two or more types selected from the group consisting of an acid catalyst, a solid base catalyst, a metal catalyst on a support, a homogeneous metal complex and a catalyst of an organic acid-alkali metal salt.

4. The process for producing 2-vinylcyclododecanone according to claim 3, wherein the acid catalyst is a Brønsted acid and/or a solid acid.

5. The process for producing 2-vinylcyclododecanone according to claim 3, wherein the solid base catalyst is (a) a catalyst on a support in which a hydroxide or carbonate of an alkali metal or alkali earth metal is carried on a support and/or (b) a metal oxide.

6. The process for producing 2-vinylcyclododecanone according to claim 3, wherein the metal catalyst on a support is ruthenium carried on a support, rhenium carried on a support, an oxidized product of ruthenium carried on a support or an oxidized product of rhenium carried on a support.

7. The process for producing 2-vinylcyclododecanone according to claim 3, wherein the homogenous metal complex is a ruthenium phosphine complex or a ruthenium phosphite complex.

8. The process for producing 2-vinylcyclododecanone according to claim 2, wherein the catalyst is one or two or more types selected from the group consisting of an acid catalyst, a solid base catalyst, a metal catalyst on a support, a homogeneous metal complex and a catalyst of an organic acid-alkali metal salt.

9. The process for producing 2-vinylcyclododecanone according to claim 8, wherein the acid catalyst is a Brønsted acid and/or a solid acid.

10. The process for producing 2-vinylcyclododecanone according to claim 8, wherein the solid base catalyst is (a) a catalyst on a support in which a hydroxide or carbonate of an alkali metal or alkali earth metal is carried on a support and/or (b) a metal oxide.

11. The process for producing 2-vinylcyclododecanone according to claim 8, wherein the metal catalyst on a support is ruthenium carried on a support, rhenium carried on a support, an oxidized product of ruthenium carried on a support or an oxidized product of rhenium carried on a support.

* * * * *

UNITED STATES PATENT AND TRADEMARK OFFICE
CERTIFICATE OF CORRECTION

PATENT NO. : 6,548,711 B2
DATED : April 15, 2003
INVENTOR(S) : Kenichi Yamamoto et al.

It is certified that error appears in the above-identified patent and that said Letters Patent is hereby corrected as shown below:

<u>Title page,</u>
Item [57], ABSTRACT, Please delete the first [Formula 1] figure.

" 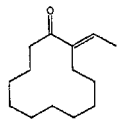 "

should be
-- [Formula 2]   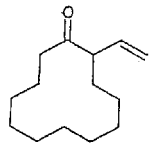   --

<u>Column 1,</u>
"   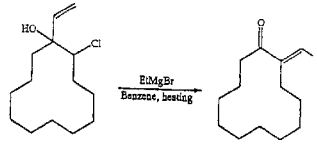   "  .

should be
-- [Formula 3]

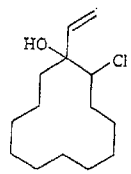   EtMgBr / Benzene, heating →   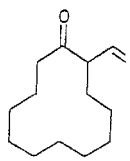

UNITED STATES PATENT AND TRADEMARK OFFICE
CERTIFICATE OF CORRECTION

PATENT NO.    : 6,548,711 B2
DATED         : April 15, 2003
INVENTOR(S)   : Kenichi Yamamoto et al.

It is certified that error appears in the above-identified patent and that said Letters Patent is hereby corrected as shown below:

Columns 1 and 2,

"
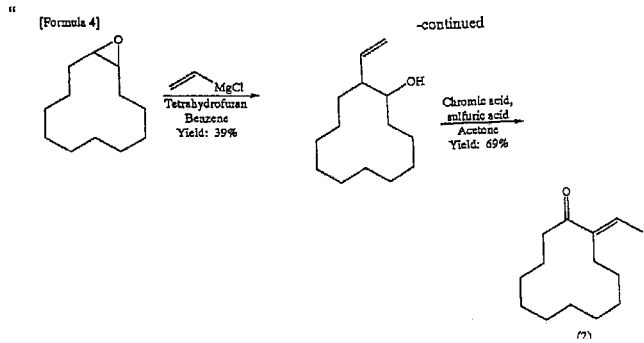
"

should be
-- [Formula 4]

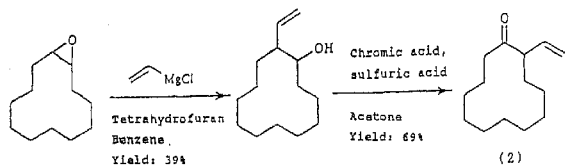

--

Column 3,

"[Formula 6]
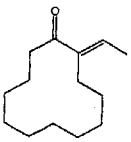
"

should be
--     [Formula 6]

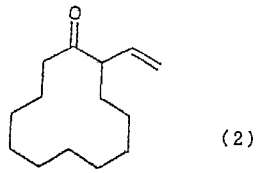

(2)

--

UNITED STATES PATENT AND TRADEMARK OFFICE
CERTIFICATE OF CORRECTION

PATENT NO. : 6,548,711 B2
DATED : April 15, 2003
INVENTOR(S) : Kenichi Yamamoto et al.

It is certified that error appears in the above-identified patent and that said Letters Patent is hereby corrected as shown below:

Column 3 cont'd,

" [Formula 7] "

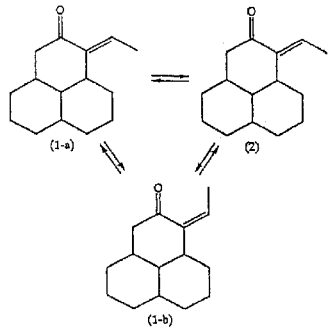

should be
-- [Formula 7]

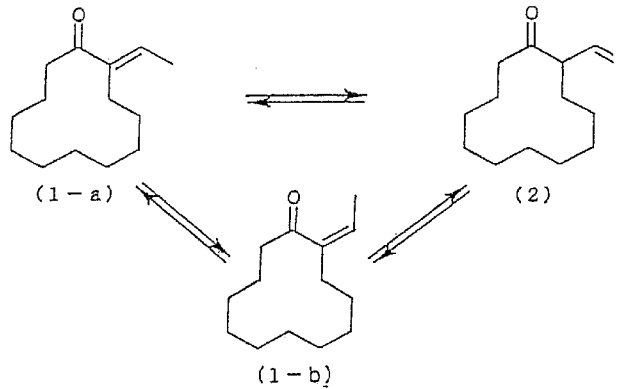

--

UNITED STATES PATENT AND TRADEMARK OFFICE
CERTIFICATE OF CORRECTION

PATENT NO. : 6,548,711 B2
DATED : April 15, 2003
INVENTOR(S) : Kenichi Yamamoto et al.

It is certified that error appears in the above-identified patent and that said Letters Patent is hereby corrected as shown below:

Column 5,

"

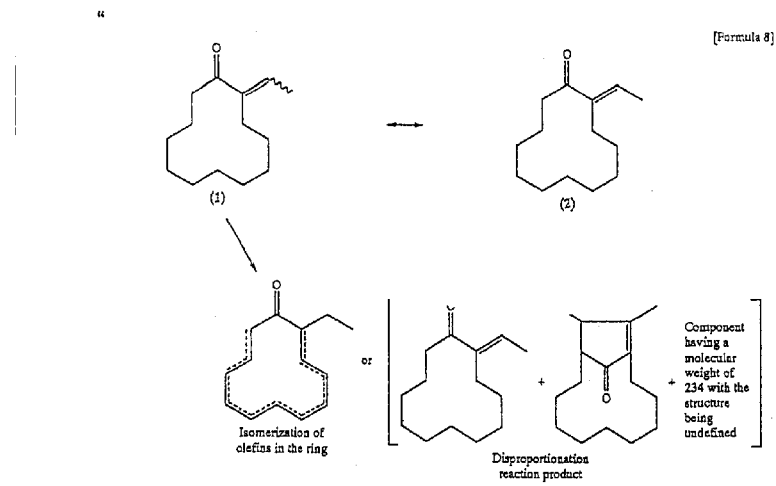

[Formula 8]

"

should be

-- [Formula 8]

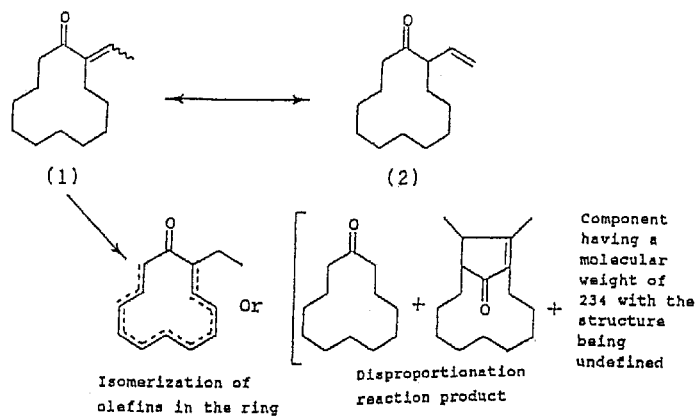

--

UNITED STATES PATENT AND TRADEMARK OFFICE
CERTIFICATE OF CORRECTION

PATENT NO. : 6,548,711 B2
DATED : April 15, 2003
INVENTOR(S) : Kenichi Yamamoto et al.

It is certified that error appears in the above-identified patent and that said Letters Patent is hereby corrected as shown below:

Column 13,
Line 5, delete the first [Formula 1] figure.

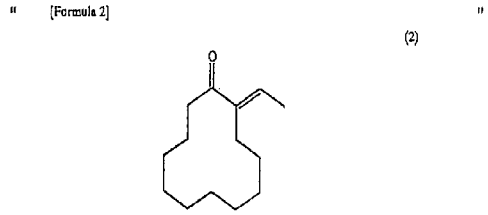

should be

-- [Formula 2] --

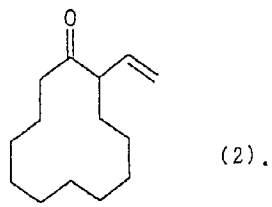

(2).

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,548,711 B2
DATED : April 15, 2003
INVENTOR(S) : Kenichi Yamamoto et al.

It is certified that error appears in the above-identified patent and that said Letters Patent is hereby corrected as shown below:

Title page,
Item [57], ABSTRACT, please delete the first [Formula 1] figure.

"
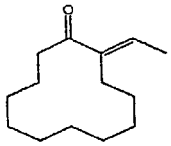
"

should be
-- [Formula 2]

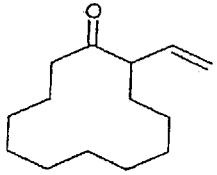
(2). --

Column 1,

"
"

should be
-- [Formula 3]

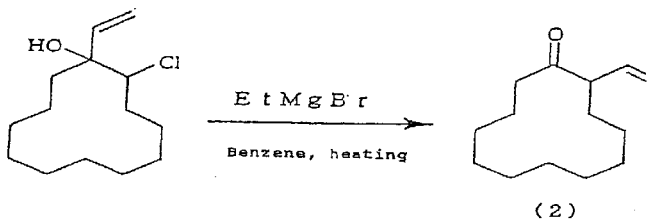
--

UNITED STATES PATENT AND TRADEMARK OFFICE
CERTIFICATE OF CORRECTION

PATENT NO.   : 6,548,711 B2
DATED        : April 15, 2003
INVENTOR(S)  : Kenichi Yamamoto et al.

It is certified that error appears in the above-identified patent and that said Letters Patent is hereby corrected as shown below:

Columns 1 and 2,

"
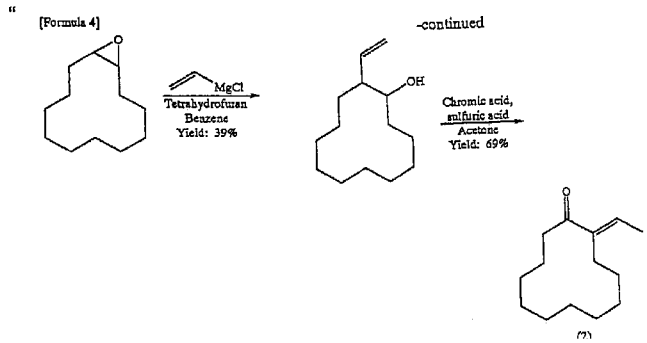
"

should be
-- [Formula 4]

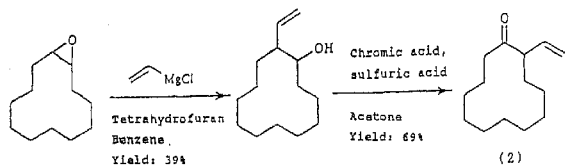

--

Column 3,

"  [Formula 6]
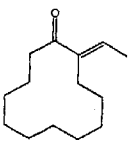
"

should be
-- [Formula 6]

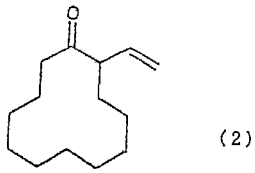

--

UNITED STATES PATENT AND TRADEMARK OFFICE
CERTIFICATE OF CORRECTION

PATENT NO.    : 6,548,711 B2  
DATED         : April 15, 2003  
INVENTOR(S)   : Kenichi Yamamoto et al.

Page 3 of 5

It is certified that error appears in the above-identified patent and that said Letters Patent is hereby corrected as shown below:

<u>Column 3 cont'd,</u>

"
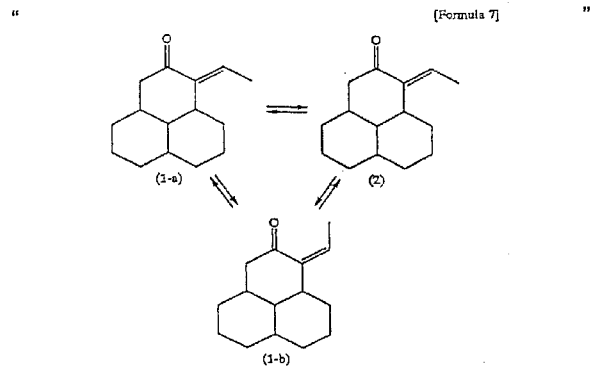
"

should be
-- [Formula 7]   --

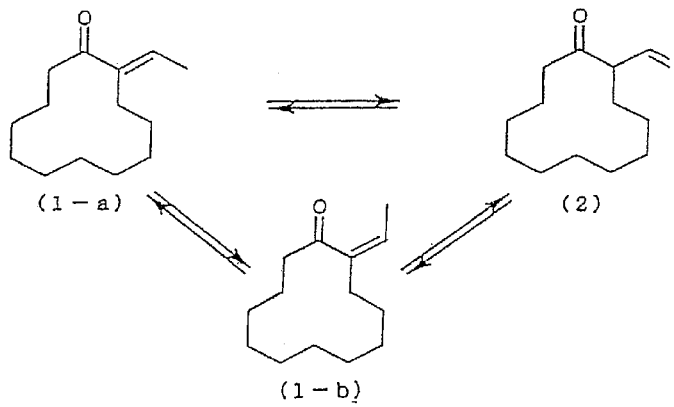

UNITED STATES PATENT AND TRADEMARK OFFICE
CERTIFICATE OF CORRECTION

PATENT NO. : 6,548,711 B2
DATED : April 15, 2003
INVENTOR(S) : Kenichi Yamamoto et al.

It is certified that error appears in the above-identified patent and that said Letters Patent is hereby corrected as shown below:

Column 5,

"

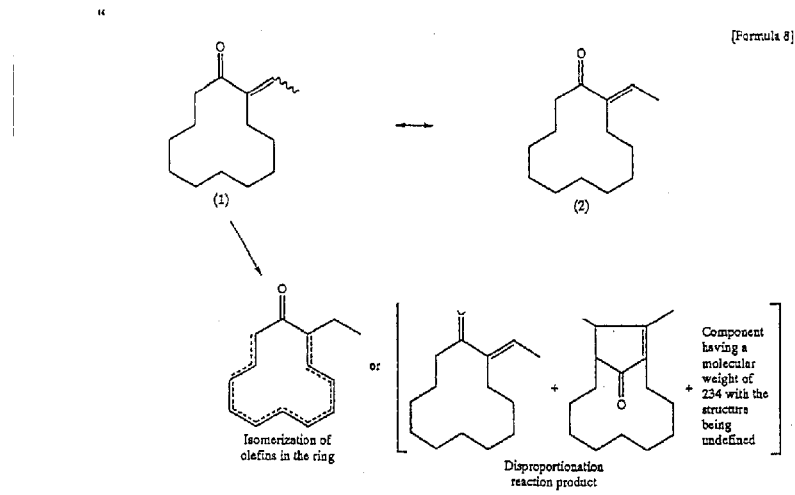

[Formula 8]

"

should be

-- [Formula 8]

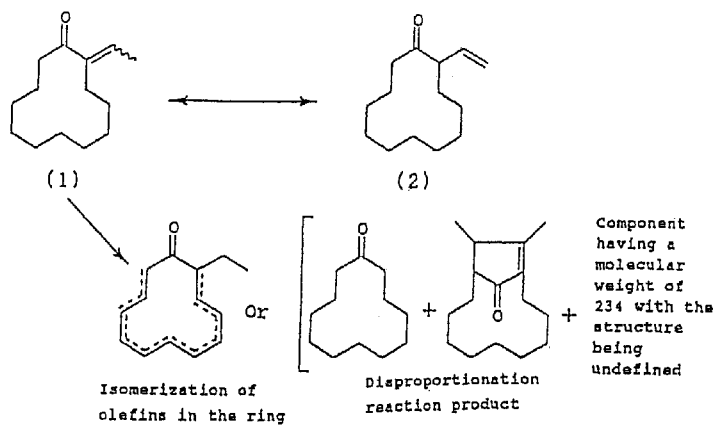

--

UNITED STATES PATENT AND TRADEMARK OFFICE
CERTIFICATE OF CORRECTION

PATENT NO. : 6,548,711 B2
DATED : April 15, 2003
INVENTOR(S) : Kenichi Yamamoto et al.

It is certified that error appears in the above-identified patent and that said Letters Patent is hereby corrected as shown below:

Column 13,
Line 5, delete the first [Formula 1] figure.

" [Formula 2] (2) "

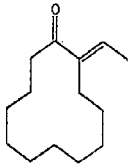

should be

-- [Formula 2] --

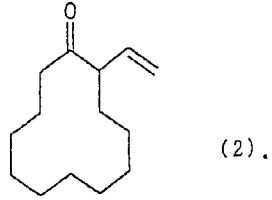

(2).

Signed and Sealed this

Twenty-first Day of October, 2003

JAMES E. ROGAN
*Director of the United States Patent and Trademark Office*